US00PP19679P2

(12) United States Plant Patent
Hambali

(10) Patent No.: US PP19,679 P2
(45) Date of Patent: Feb. 10, 2009

(54) ***AGLAONEMA* PLANT NAMED 'TWYAG0001'**

(50) Latin Name: *Aglaonema commutatum×A.rotundum* hybrid
Varietal Denomination: TWYAG0001

(75) Inventor: Gregori Garnadi Hambali, Bogor (ID)

(73) Assignee: Kerry's Bromeliad Nursery, Inc., Apopka, FL (US)

( * ) Notice: Subject to any disclaimer, the term of this patent is extended or adjusted under 35 U.S.C. 154(b) by 0 days.

(21) Appl. No.: 11/903,065

(22) Filed: Sep. 20, 2007

(51) Int. Cl.
*A01H 5/00* (2006.01)

(52) U.S. Cl. ..... Plt./376
(58) Field of Classification Search ..... Plt./376
See application file for complete search history.

*Primary Examiner*—Anne Marie Grunberg
*Assistant Examiner*—Louanne C Krawczewicz My
(74) *Attorney, Agent, or Firm*—Jondle & Associates, P.C.

(57) ABSTRACT

A new *Aglaonema* plant particularly distinguished by being intermediate in stature, having a leafy, compact, upright, vigorous growth habit, excellent indoor keeping quality and having a somewhat faster growth rate than typical commercial *Aglaonema* cultivars, is disclosed.

2 Drawing Sheets

Genus and species: *Aglaonema commutatum×A. rotundum* hybrid.
Variety denomination: 'TWYAG0001'.

BACKGROUND OF THE NEW PLANT

The present invention comprises a new and distinct cultivar of *Aglaonema,* botanically known as *Aglaonema commutatum×A. rotundum* hybrid, and hereinafter referred to by the cultivar name 'TWYAG0001'. The new cultivar originated from an open pollination made in Bogor, W. Java, Indonesia. A cross was made in October 2000 and a single plant was selected for further evaluation and asexual propagation in August 2002.

The new cultivar was created in Bogor, W. Java, Indonesia and has been asexually reproduced repeatedly by vegetative cuttings and tissue culture in Apopka, Fla. The present invention has been found to retain its distinctive characteristics through successive asexual propagations.

Plant Breeder's Rights for this cultivar were applied for in the European Union in early September 2007. 'TWYAG0001' has not been made publicly available more than one year prior to the filing of this application.

SUMMARY OF THE INVENTION

The following are the most outstanding and distinguishing characteristics of this new cultivar when grown under normal horticultural practices in Apopka, Fla.

1. Intermediate in stature;
2. Leafy, compact and upright branched growth habit;
3. Vigorous;
4. Excellent indoor keeping quality; and
5. Somewhat more rapid growth rate than typical commercial *Aglaonema* cultivars.

DESCRIPTION OF PHOTOGRAPHS

This new *Aglaonema* plant is illustrated by the accompanying photographs which show overall plant habit and leaves. The colors shown are as true as can be reasonably obtained by conventional photographic procedures.

DESCRIPTION OF THE NEW CULTIVAR

Figure 1:
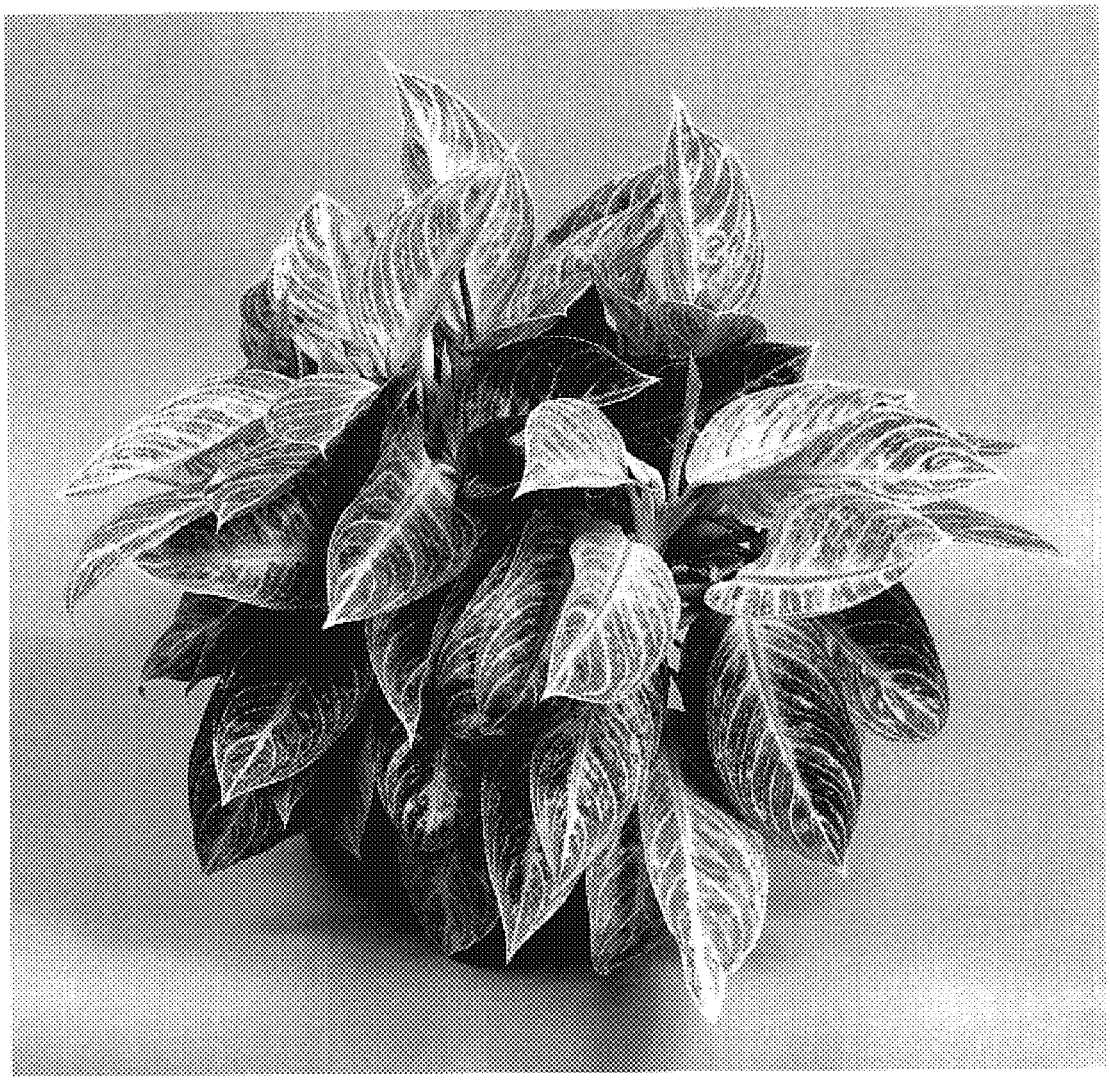
FIG. 1 shows the overall plant habit.
Figure 2:
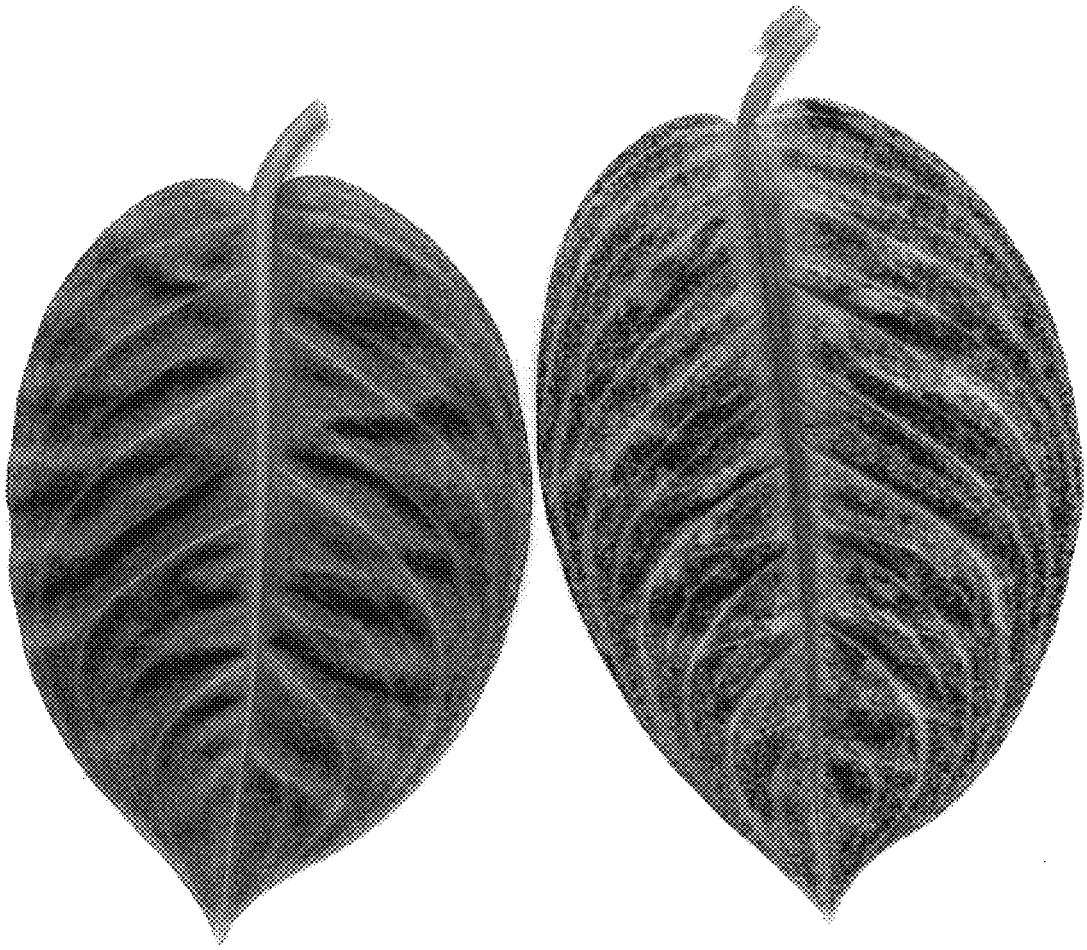
FIG. 2 shows the upper and lower surface of a mature leaf.

The following detailed description sets forth the distinctive characteristics of 'TWYAG0001'. The data which define these characteristics were collected from asexual reproductions carried out in Apopka, Fla. The plant history was taken on 18-month-old plants started from a single 4-leaf rooted cutting, still in a vegetative state and grown in Apopka, Fla. Rooted cuttings were planted in 20-cm pots and grown in a greenhouse in July 2006. The average daily temperature was about 85° to 95° F. and the average nightly temperature was about 72° to 78° F. The light level was about 1500 to 3000 foot candles. The plants were pinched twice. Color readings were taken under natural light. Color references are primarily to the R.H.S. Colour Chart of The Royal Horticultural Society of London (R.H.S.) (2001).

DETAILED BOTANICAL DESCRIPTION

Classification:
- *Family.*—Araceae.
- *Botanical.*—*Aglaonema* hybrid.
- *Cultivar name.*—'TWYAG0001'.
- *Common name.*—Chinese evergreen.

Parentage: Unknown individual plant of *A. commutatum* and unknown individual plant of *A. rotundum*

Growth:
- *Form.*—Symmetrical, new leaves held upright, mature leaves arch outward.
- *Growth and branching habit.*—Leafy and compact; upright, branched growth habit (basal branching); intermediate in stature.
- *Height* (*from soil to top of leaf plane*).—36 cm to 41 cm.
- *Diameter* (*area of spread, measured from leaf tip to leaf tip across the canopy*).—44 cm to 50 cm.

*Time to produce a finished flowering plant.*—18 months starting from a single four-leaf rooted cutting and pinched twice.

*Root description.*—Abundant, fleshy white roots with finer lateral branches.

*Number of divisions or clumps per year.*—About 10 to 13 four-leaf cuttings per year.

*Durability of foliage to stresses.*—Leaves hold up well against damage from shipping and handling; plant is durable, excellent indoor keeping quality.

*High temperature tolerance.*—To about 104° F. for several hours without damage.

*Low temperature tolerance.*—To about 55° F. for several hours without damage.

Stems:

*Type.*—Basal branching.

*Number of branches per plant.*—27.

*Length (from soil line to the junction of the newest two leaves).*—20 cm.

*Diameter (measured from the midpoint).*—0.90 cm.

*Internode length.*—1.25 cm to 2.0 cm.

*Color.*—Immature: RHS 155D tinged with RHS 160D. Mature: RHS 161C with areas of RHS 160D. Oldest stems: RHS 161D tinged with RHS 160B.

*Appearance (shape).*—Columnar, cylindrical upright.

*Aspect.*—Vertical, upright.

*Strength.*—Sturdy, somewhat flexible.

*Axillary buds.*—Shape: Elliptic, flat. Length: 0.4 cm. Width: 0.22 cm. Color: RHS 155D.

Leaves:

*Arrangement.*—Alternate, single leaf per petiole, simple arranged in a spiral along the stem.

*Quantity of leaves per stem.*—10.

*Length.*—15.0 cm to 17.0 cm.

*Width.*—Flattened: 8.5 cm to 9.7 cm. Not flattened: 6.5 cm to 7.8 cm; leaf blade folds upward along the midrib.

*Shape.*—Ovate.

*Apex.*—Acuminate.

*Base.*—Cordate to obtuse.

*Margin.*—Smooth, entire with some broad undulations.

*Texture.*—Upper surface: Smooth; new leaves shiny; mature leaves glossy; Lower Surface: Smooth, new leaves glossy; mature leaves glossy to dull; the leaf blade is convex between the main veins resulting in a textured appearance.

*Pubescence.*—None.

*Young leaf (newly expanded leaf).*—Color: Upper side: Between RHS 147A and RHS 146A base color with small coalescing spots and blotches of RHS 145D and RHS 158D; areas adjacent to the primary veins and midrib marked with small coalescing spots and blotches of RHS 158D often variably tinged with RHS 49D. Under side: Between RHS 181C and RHS 181D base color mottled with RHS 147A; upper side pattern and markings visible through the underside; areas adjacent to the primary veins and midrib RHS 181C to RHS 181D.

*Mature leaf.*—Color: Upper side: RHS 147A base color suffused with small coalescing spots and blotches of RHS 145C to RHS 145D occasionally variably tinged with RHS 49C to RHS 49D; areas adjacent to the primary veins and midrib marked with small coalescing spots and blotches of RHS 145C to RHS 145D, flushed with RHS 50B to RHS 50C. Under side: RHS 181B to RHS 181C mottled with RHS 147A; upper side pattern and markings visible through the underside; areas adjacent to the primary veins and midrib RHS 181B to RHS 181C.

*Venation pattern.*—Pinnate, radiating outward from the midrib in a herringbone arrangement.

*Venation color (newly expanded leaf).*—Upper side: Primary veins: RHS 158B. Midrib-distal: RHS 49C to RHS 49D with streaks of RHS 146B. Midrib-proximal: RHS 49C to RHS 49D tinged with RHS 51D, with streaks of RHS 146B. Under side: Primary veins: RHS 181D. Midrib: RHS 50C.

*Venation color (mature leaf).*—Upper side: Primary veins: RHS 49A to RHS 49B. Midrib: RHS 50A to RHS 50B streaked with RHS 146B (green). Under side: Primary veins: RHS 181D. Midrib: RHS 51B.

Petioles:

*Aspect.*—Vertical upright when newly expanded, becoming curved outward and about 45° with maturity.

*Length.*—8.5 cm.

*Diameter.*—Distal: 0.4 cm. Proximal (petiole and petiole sheath clasps the stem proximally): Flattened: 2.8 cm. Natural diameter: 0.90 cm.

*Color.*—Distal: RHS 51B to RHS 51C (between the top of the wing and the base of the leaf). Proximal: RHS 49C to RHS 49D streaked with RHS 50B to RHS 50C. Area adjacent to stem: RHS 159D.

*Wing length.*—6.8 cm.

*Wing diameter.*—Mid-point: 0.7 cm. Base: 0.90 cm. Depth: 0.55 cm.

*Wing color.*—Inside: RHS 49D. Outside: RHS 49C to RHS 49D flushed with RHS 50B to RHS 50C. Area adjacent to stem: RHS 159D.

*Cataphylls.*—Length: 5.5 cm. Width: 1.8 cm. Shape: Linear to lanceolate, two keeled, translucent. Apex: Cuspidate. Base: Clasps the peduncle. Texture: Inside: Smooth, shiny. Outside: Glossy. Color: Proximal: RHS 155D. Distal: RHS 50C.

Inforescence:

*Type.*—Hooded flower spathes surrounding a columnar spadix borne atop an upright peduncle; monoecious; spadix a central column of sessile, simple male and female flowers separated into two zones; male flowers occupy the upper two-thirds of the spadix while female flowers occupy the lower one-third of the spadix.

*Arrangement.*—3 inflorescences per stem, persistent.

*Aspect.*—Upright.

*Height (from base of peduncle to tip of spathe).*—14.5 cm.

*Diameter/width.*—6.0 cm.

*Flowering habit.*—Seasonal, summer and fall as observed in Apopka, Fla.

*Number of inflorescences per plant.*—5.

*Fragrance.*—None.

*Ratio of inflorescence opening.*—About 1 new inflorescence every 10–14 days.

*Lastingness of inflorescences.*—Not observed.

*Peduncle.*—Length: 8.9 cm to 11.4 cm. Diameter: 0.38 cm. Angle: Upright. Strength: Sturdy, flexible. Color: Distal: RHS 49B to RHS 49D variably marked with RHS 144C. Proximal: RHS 155D.

Spathe:

*Appearance.*—Simple, hooded, cupped, enclosing spadix.

*Aspect.*—Upright.

*Shape.*—*Elliptic.*
*Apex.*—Acute.
*Base.*—Acute to obtuse.
*Margin.*—Entire.
*Texture.*—Smooth, shiny.
*Size.*—Length: 6.6 cm. Width: 2.0 cm.
*Color.*—When opening: Front side: Distal: RHS 160B to RHS 160C. Proximal: RHS 155D. Rear side (distal): RHS 160B to RHS 160C variably mottled or streaked with RHS 146D. Fully opened: Front side: Distal: RHS 160D. Proximal: RHS 155D. Rear side: Distal: RHS 160C to RHS 160D variably mottled or streaked with RHS 146D. Apex: RHS 146D.

Spadix:
*Size.*—Length: 3.4 cm. Diameter (female zone): 0.7 cm. Diameter (male zone): 0.6 cm. Length of female zone: 0.65 cm. Length of male zone: 2.7 cm.
*Appearance.*—Columnar.
*Aspect.*—Upright.
*Shape.*—Columnar.
*Apex.*—Obtuse.
*Base.*—Obtuse.
*Margin.*—Pebbled.
*Color.*—Female zone: RHS 9C. Male zone: RHS 8D.

Flowers:
*Type.*—Simple, individual flowers reduced to the most basic elements.
*Quantity of female flowers per spadix.*—20.
*Quantity of male flowers per spadix.*—250.
*Shape of female.*—Ovate to elliptic.
*Shape of male.*—Obovate, inverted triangle.
*Size.*—Female width: 0.2 cm. Female height: 0.2 cm. Male width: 0.15 cm. Male height: 0.2 cm.

Reproductive organs:
*Stigma color.*—RHS 9C.
*Ovary color.*—RHS 158C.

Fruit and seed set: None observed.

Disease and insect resistance: Typical of *Aglaonema;* no particular susceptibility or resistance to pests or diseases noted.

COMPARISON WITH OTHER KNOWN CULTIVARS

'TWYAG0001' differs from the commercial variety 'Dynamic Ruby' (U.S. Plant Pat. No. 14,137) in that 'TWYAG0001' has a larger growth habit than 'Dynamic Ruby' and lacks fragrance whereas 'Dynamic Ruby' has fragrance.

I claim:

1. A new and distinct cultivar of *Aglaonema* plant as shown and described herein.

* * * * *